(12) United States Patent
Seehra et al.

(10) Patent No.: US 8,772,234 B2
(45) Date of Patent: *Jul. 8, 2014

(54) BMP10 PROPEPTIDES AND RELATED METHODS

(75) Inventors: Jasbir Seehra, Lexington, MA (US); John Knopf, Carlisle, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,479

(22) Filed: Apr. 9, 2012

(65) Prior Publication Data

US 2012/0213782 A1 Aug. 23, 2012

Related U.S. Application Data

(63) Continuation of application No. 12/316,083, filed on Dec. 9, 2008, now Pat. No. 8,287,868, which is a continuation of application No. 11/128,937, filed on May 12, 2005, now Pat. No. 7,741,284.

(60) Provisional application No. 60/570,779, filed on May 12, 2004.

(51) Int. Cl.
*A61K 38/16* (2006.01)
*A61K 38/18* (2006.01)
*C07K 14/51* (2006.01)
*C12N 15/09* (2006.01)

(52) U.S. Cl.
USPC ........... 514/8.8; 514/21.2; 530/399; 435/69.7

(58) Field of Classification Search
None
See application file for complete search history.

(56) References Cited

U.S. PATENT DOCUMENTS

| | | | |
|---|---|---|---|
| 5,637,480 | A | 6/1997 | Celeste et al. |
| 5,808,007 | A | 9/1998 | Lee et al. |
| 5,834,179 | A | 11/1998 | Jones et al. |
| 6,004,780 | A | 12/1999 | Soppet et al. |
| 6,071,708 | A | 6/2000 | Jones et al. |
| 6,656,708 | B1 | 12/2003 | Yu et al. |
| 2002/0137143 | A1 | 9/2002 | Soppet et al. |
| 2003/0082233 | A1 | 5/2003 | Lyons et al. |
| 2003/0144176 | A1 | 7/2003 | Olson et al. |
| 2003/0224501 | A1* | 12/2003 | Young et al. .................. 435/226 |
| 2005/0244867 | A1 | 11/2005 | Soppet et al. |

FOREIGN PATENT DOCUMENTS

| | | |
|---|---|---|
| WO | WO 94/03600 A1 | 2/1994 |
| WO | WO 94/15965 A1 | 7/1994 |
| WO | WO 94/26893 A1 | 11/1994 |
| WO | WO 95/24474 A1 | 9/1995 |
| WO | WO 96/39431 A1 | 12/1996 |
| WO | WO 99/37320 A1 | 7/1999 |
| WO | WO 00/43781 A2 | 7/2000 |
| WO | WO 01/92298 A2 | 12/2001 |
| WO | WO 02/43759 A2 | 6/2002 |
| WO | WO-03/022998 A2 | 3/2003 |

OTHER PUBLICATIONS

Beiboer, S., et al., "Guided selection of a Pan carcinoma specific antibody reveals similar binding characteristics yet structural divergence between the original murine antibody and its human equivalent," J. Mol. Biol., 296:833-849 (2000).
Bork, P., "Powers and pitfalls in sequence analysis: the 70% hurdle," Genome Research, 10:398-400 (2000).
Brenner, S., "Errors in genome annotation," Trends in Genetics, 15(4):132-133 (1999).
Caricasole, A.A.D., et al., "Human growth-differentiation factor 3 (hGDF3): developmental regulation in human teratocarcinoma cell lines and expression in primary testicular germ cell tumours," Oncogene, 16:95-103 (1998).
Chen, H., et al., "BMP10 is essential for maintaining cardiac growth during murine cardiogenesis," Development, 131(9):2219-2231 (2004).
Chen, H., et al., "Overexpression of Bone Morphogenetic Protein 10 in Myocardium Disrupts Cardiac Postnatal Hypertrophic Growth," Journal of Biological Chemistry, 281(37):27481-27491 (2006).
Clark, A.T., et al., "Human Stellar, Nanog, and GDF3 Genes are Expressed in Pluripotent Cells and Map to Chromosome 12p13, a Hotspot for Teratocarcinoma," Stem Cells, 22:169-179 (2004).
Constam, D.B., et al., "Regulation of Bone Morphogenetic Protein Activity by Pro Domains and Proprotein Convertases", The Journal of Cell Biology, 144(1):139-149 (1999).
Daluiski, A., et al., "Bone Morphogenetic Protein-3 is a Negative Regulatory of Bone Density," Nature Genetics, 27(1):84-88 (2001).
Doerks, T.,et al., "Protein annotation: detective work for function prediction," Trends in Genetics, 14(6):248-250 (1998).
Faucheux, C., et al., "Opposing Actions of BMP3 and TGFbetal in Human Bone Marrow Stromal Cell Growth and Differentiation," Biochemical and Biophysical Research Communications, 241(3):787-793 (1997).
Graddis, T.J., et al., "Designing proteins that work using recombinant technologies," Curr. Pharm. Biotechnol. 3:285-297 (2002).
Hino, J., et al., "Bone Morphogenetic Protein-3 Family Members and Their Biological Functions," Frontiers in Bioscience, 9:1520-1529 (2004).
Hino, J., et al., "Bone Morphogenetic Protein-3B (BMP-3B) Gene Expression is Correlated with Differentiation in Rat Calvarial Osteoblasts," Biochemical and Biophysical Research Communications, 256(2):419-424 (1999).
Hino, J., et al., "Coordination of BMP-3b and cerebus is required for head formation of Xenopus embryos", Developmental Biology, 260(1):138-157 (2003).

(Continued)

Primary Examiner — Xiaozhen Xie
(74) Attorney, Agent, or Firm — Ropes & Gray LLP

(57) ABSTRACT

In certain aspects, the present invention provides BMP10 propeptides for use in treating a variety of disorders including heart disorders and other disorders associated with unwanted activity of the mature BMP10 polypeptide. The present invention also provides methods of screening compounds that modulate activity of BMP10.

10 Claims, 10 Drawing Sheets

(56) References Cited

OTHER PUBLICATIONS

Kirsch, T., et al., "BMP-2 antagonists emerge from altercations in the low-affinity binding epitope for receptor BMPR-II," EMBO Journal, 19(13):3314-3324 (2000).

Klimka, A., et al., "Human anti-CD30 recombinant antibodies by guided phage antibody selection using cell panning," British Journal of Cancer, 83:252-260 (2000).

MacCallum, R., et al., "Antibody-antigen Interactions: Contact Analysis and Binding Site Topography," J. Mol. Biol., 262:732-745 (1996).

McPherron, A.C., et al., "GDF-3 and GDF-9: two new members of the transforming growth factor-beta superfamily containing a novel pattern of cysteines," *Journal of Biological Chemistry*, 268(5):3444-3449 (1993).

Nagaso, H., et al., "Dual Specificity of Activin Type II Receptor ActRIIb in Dorso-Ventral Patterning During Zebrafish Embryogenesis," Development Growth and Differentiation, 41(2)119-133 (1999).

Neuhaus, H., et al., "Heart specific expression of mouse *BMP*-10 a novel member of the TGF-β superfamily," Mechanisms of Development, 80:181-184 (1999).

Ngo, J.T., et al., "Computational complexity, protein structure prediction, and the Levinthal paradox. The Protein Folding Problem and Tertiary Structure Prediction," pp. 491-495 (1995).

Pashmforoush, M., et al., "Nkx2-5 Pathways and Congenital Heart Disease: Loss of Ventricular Myocyte Lineage Specification Leads to Progressive Cardiomyopathy and Complete Heart Block," Cell, 117:373-386 (2004).

Skolnick, J., et al., "From genes to protein structure and function: novel applications of computational approaches in the genomic era," Trends in Biotech. 18(1):34-39 (2000).

Smith, T., et al., The challenges of genome sequence annotation or "the devil is in the details," Nature Biotech, 15:1222-1223 (1997).

Srivastava, D., "An Ongoing Genetic Battle?" Nature, 429:819-822 (2004).

Takao, M., et al., "Identification of Rat Bone Morphogenetic Protein-3b (BMP-3b), a New Member of BMP-3," Biochemical and Biophysical Research Communications, 219(2)656-662 (1996).

Teichmann, U., et al., "Highly restricted BMP10 expression in the trabeculating myocardium of the chick embryo," Dev Genes Evol., 214:96-98 (2004).

Thies, R.S., et al., "GDF-8 Propeptide Binds to a GDF-8 and Antagonizes Biological Activity by inhibiting GDF-8 Receptor Binding," Growth Factors, 18:251-259 (2001).

Wang, W., et al., "GDF-3 is an adipogenic cytokine under high fat dietary condition," *Biochemical and Biophysical Research Communications*, 321:1024-1031 (2004).

Wells, J., "Additivity of mutational effects in proteins," Biochemistry, 29(37):8509-8517 (1990).

Witthuhn, B.A., et al., "Upregulation of Bone Morphogenetic Protein GDF-3/Vgr-2 Expression in Adipose Tissue of FABP4/aP2 Null Mice," *Cytokine*, 14:129-135 (2001).

\* cited by examiner

Figure 1. Human BMP10 propeptide sequence designated as SEQ ID NO: 1 (295 aa).

SPIMNLEQSPLEEDMSLFGDVFSEQDGVDFNTLLQSMKDEFLKTINLSDIPTQDSAKVD

PPEYMLELYNKFATDRTSMPSANIIRSFKNEDLFSQPVSFNGLRKYPLLFNVSIPHHEE

VIMAELRLYTLVQRDRMIYDGVDRKITIFEVLESKGDNEGERNMLVLVSGEIYGTNSEW

ETFDVTDAIRRWQKSGSSTHQLEVHIESKHDEAEDASSGRLEIDTSAQNKHNPLLIVFS

DDQSSDKERKEELNEMISHEQLPELDNLGLDSFSSGPGEEALLQMRSNIIYDSTARIRR

Figure 2. Mouse BMP10 propeptide sequence designated as SEQ ID NO: 2 (291 aa).

SPIMGLEQSPLEEDMPFFDDIPTEQDGIDFNTLLQSMKNEFLKTLNLSDIPVQDTGRVD

PPKYMLELYNKFATDRTSMPSANIIRSFKNELFSQPVTFNGLRKYPLLFNVSIPHHEEV

VMAELRLYTLVQRDRMMYDGVDRKITIPEVLESADGSEEERSMLVLVSTEIYGTNSEWE

TFDVTDATRRWQKSGPSTHQLEIHIESRQNQAEDTGRGQLEIDMSAQNKHDPLLVVFSD

DQSNDKEQKEELNELITHEQDLDLDSDAFFSGPDREALLQMRSNMIDDSSTRIRR

Figure 3. Human BMP10 precursor sequence designated as SEQ ID NO: 3 (NP_055297, 424 aa).

MGSLVLTLCALFCLAAYLVSGSPIMNLEQSPLEEDMSLFGDVFSEQDGVDFNTLLQSMK

DEFLKTLNLSDIPTQDSAKVDPPEYMLELYNKFATDRTSMPSANIIRSFKNEDLFSQPV

SFNGLRKYPLLFNVSIPHHEEVIMAELRLYTLVQRDRMIYDGVDRKITIFEVLESKGDN

EGERNMLVLVSGEIYGTNSEWETFDVTDAIRRWQKSGSSTHQLEVHIESKHDEAEDASS

GRLEIDTSAQNKHNPLLIVFSDDQSSDKERKEELNEMISHEQLPELDNLGLDSFSSGPG

EEALLQMRSNIIYDSTARIRR

Figure 4. Mouse BMP10 precursor sequence designated as SEQ ID NO: 4 (NP_033886, 420 aa).

MGSLVLPLSAVFCLVAHSASGSPIMGLEQSPLEEDMPFFDDIFTEQDGIDFNTLLQSMK

NEFLKTLNLSDIPVQDTGRVDPPKYMLELYNKFATDRTSMPSANIIRSFKNELFSQPVT

FNGLRKYPLLFNVSIPHHEEVVMAELRLYTLVQRDRMMYDGVDRKITIFEVLESADGSE

EERSMLVLVSTEIYGTNSEWETFDVTDATRRWQKSGPSTHQLEIHIESRQNQAEDTGRG

QLEIDMSAQNKHDPLLVVFSDDQSNDKEQKEELNELITHEQDLDLDSDAFFSGPDEEAL

LQMRSNMIDDSSTRIRR

Figure 5. Nucleic acid sequence encoding a human BMP10 propeptide, designated as SEQ ID NO: 5 (885 bp).

```
agcccatcatgaacctagagcagtctcctctggaagaagatatgtccctcttttggtgatgttttctcaga
gcaagacggtgtcgacttttaacacactgctccagagcatgaaggatgagttttcttaagacactaaacctct
ctgacatcccacgcaggattcagccaaggtggacccaccagagtacatgttggaactctacaacaaatttt
gcaacagatcggacctccatgccctctgccaacatcattaggagtttcaagaatgaagatctgttttccca
gccggtcagttttaatggctccgaaaatacccctcctcttcaatgtgtccattcctcaccatgaagagg
tcatcatggctgaacttaggctatacaacactggtgcaaaggatcgtatgatatacgatggagtagaccgg
aaaattaccattttttgaagtgctggagagcaaaggggataatgagggagaaagaaacatgctggtcttggt
gtctggggagatatatggaaccaacagtgagtgggagacttttgatgtcacagatgccatcagacgttggc
aaaagtcaggctcatccaccaccagctggaggtccacattgagagcaaacacgatgaagctgaggatgcc
agcagtggacggctagaaatagataccagtgcccagaataagcataaccctttgctcatcgtgttttctga
tgaccaaagcagtgacaaggagaggaaggaggaactgaatgaaatgatttcccatgagcaacttccagagc
tggacaacttgggcctggatagcttttccagtggacctggggaagaggctttgttgcagatgagatcaaac
atcatctatgactccactgcccgaatcagaagg
```

Figure 6. Nucleic acid sequence encoding a mouse BMP10 propeptide, designated as SEQ ID NO: 6 (873 bp).

```
agcccattatgggcttgagcagtcgccctggaagaagacatgcccttctttgatgatatcttcacgga
gcaagatggtattgacttcaacacactgctgcagagcatgaagaacgagtttctcaagacgctgaacttgt
cggacattcctgtgcaggacacgggcagagtggatccaccaagtacatgctggagctctacaacaaatto
gccacagaccggacctccatgccgtctgctaacatcatccggagcttcaagaacgaactgtttctcaacc
agtcacttttaatgggctccggaaatatcctctcctcttcaatgtgtctatcctcaccatgaagaggtcg
tcatggctgaactgcggttgtacacgctggtgcagagagatcgcatgatgtatgatggcgtggacgtaaa
attaccattttgaggtactagagagtgcagacggtagcgaggaggagaggagcatgctggtcttagtatc
aacagagatctacggaaccaacagtgagtgggagacatttgacgtcacagatgccaccagacgttggcaaa
agtcaggcccatcaacccatcagctggagatccacatagaaagcagacaaaaccaagctgaggacacgga
aggggacaactggaaatagatatgagtgcccaaaataagcatgacccctttgctggttgtgttttctgatga
ccaaagcaatgacaaggagcagaagaagaactgaacgaattgatcacccatgagcaggatctggacctgg
actcagatgctttcttcagtgggccgatgaagaggctctgctgcagatgaggtcgaacatgattgatgat
tcgtccactcggatcaggagg
```

Figure 7. Nucleic acid sequence encoding a human BMP10 precursor protein, designated as SEQ ID NO: 7 (nucleotides 160-1431 of NM_014482, 1272 bp).

atgggctctctggtcctgacactgtgcgctctttctgctggcagcttacttggtttctggcagcccat
catgaacctagagcagtctcctctggaagaagatatgtccctctttggtgatgttttctcagagcaagacg
gtgtcgactttaacacactgctccagagcatgaaggatgagtttcttaagacactaaacctctctgacatc
cccacgcaggattcagccaaggtggacccaccagagtacatgttggaactctacaacaaattgcaacaga
tggacctccatgccctctgcaacatcattaggagtttcaagaatgaagatctgtttttccagccggtca
gtttta atgggctccgaaaata cccctctctcttcaatgtgtccattcctcaccatgaagaggt catcatg
gctgaactaggctatacacactggtgcaaagggatcgtatgatatacgatggagtagaccggaaaattac
cattttgaagtgctggagagcaaaggggataatgagggagaagaaacatgctggtcttggtgtctgggg
agatatatggaaccaacagtgagtggagactttt gatgtcacagatgccatcagacgttggcaaaagtca
ggctcatccacccaccagctggaggtccacattgagagcaaacacgatgaagctgaggatgccagcagtgg
acggctagaaatagataccagtgcccagaataagcataaccctttgctcatcgtgtttctgatgaccaaa
gcagtgacaaggagaggaaggaggaactgaatgaaatgatttcccatgagcaacttccagagctggacaac
ttgggcctggatagcttttccagtggacctggggaagaggctttgttgcagatgagatcaaacatcatcta
tgactccactgcccgaatcagaaggaacgccaaaggaaactactgtaagaggacccgctctacatcgact
tcaaggagattgggtgggactcctggatcatcgctccgctggatacgaagcctatgaatgccgtggtgtt
tgtaactaccccctggcagagcatctcacaccccacaaagcatgcaattatccaggccttggtccacctcaa
gaattcccagaaagcttccaaagcctgctgtgtgcccacaaagctagagcccatctccatcctctatttag
acaaaggcgtcgtcacctacaagtttaaatacgaaggcatggccgtctccgaatgtggctgtaga Figure 8. Nucleic acid sequence encoding a mouse BMP10 precursor protein, designated as SEQ ID NO: 8 (nucleotides 1-1260 of NM_009756, 1260 bp).

```
atggggtctctggttctgccgctgagcgccgtcttctgcctggtggctcactcggctctggcagcccat
tatgggcttgagcagtcgccctggaagaagacatgccttctttgatgatatcttcacggagcaagatg
gtattgactcaacacactgctgcagagcatgaagaacgagtttctcaagacgctgaacttgtcggacatt
cctgtcaggacacgggagagtggatccaccaagtacatgctggagctctacaacaaattcgccacaga
cggacctccatgccgtctgtaacatcatcggagcttcaagaacgaactgttttctcaaccagtcactt
ttaatgggctcggaaatatcctctcctcttcaatgtgtctatcctcaccatgaagaggtcgtcatggct
gaactgcggttgtacacgctggtgcagagagatgcatgatgtatgatggcgtggacgtaaaattaccat
ttttgaggtactagagagtgcagacggtagcgaggaggagaggagcatgctggtcttagtatcaacagaga
tctacggaaccaacagtgagtgggagacatttgacgtcacagatgccaccagacgttggcaaaagtcaggc
ccatcaaccatcagctggagatccacatagaaagcagacaaaaccaagctgaggacacggaagggaca
actggaaatagatatgagtgcccaaaataagcatgacccttttgctggttgtgtcttctgatgaccaaagca
atgacaaggagcagaaagaagaactgaacgaattgatcaccatgagcaggatctggacctggactcagat
gcttcttcagtgggccgatgaagaggctctgctgcagatgaggtcgaacatgattgatgattcgtccac
tcggatcaggaggaacgccaaggggaactactgtaagaagaccccactatacatcgacttcaaggagattg
ggtgggactcctggatcatcgtcctcctgggtatgaagccatgagtgccggggtgtgtaactaccct
ctggcggagcacctcacacctacaaacacgaattattcaggcctggtccacctcaaggattccagaa
agcttccaaagctgctgtgtgcccacgaagctggatccatctccatcctctatttagataaaggtgtcg
tcacctacaagtttaaatatgaagggatggctgtgtctgagtgtggctgtaga
```

Figure 9. Human Fc sequence. Certain useful mutations are shown in bold.

THTCPPCPAPELLGGPSVFLFPPKPKDTLMISRTPEVTCVVVD (A) VSHEDPEV
KFNWYVDGVEVHNAKTKPREEQYNSTYRVVSVLTVLHQDWLNGKEYKCK (A) VS
NKALPVPIEKTISKAKGQPREPQVYTLPPSREEMTKNQVSLTCLVKGFYPSDIA
VEWESNGQPENNYKTTPPVLDSDGPFFLYSKLTVDKSRWQQGNVFSCSVMHEAL
HN (A) HYTQKSLSLSPGK*

Figure 10: BMP10 Propeptide Binds to BMP-10
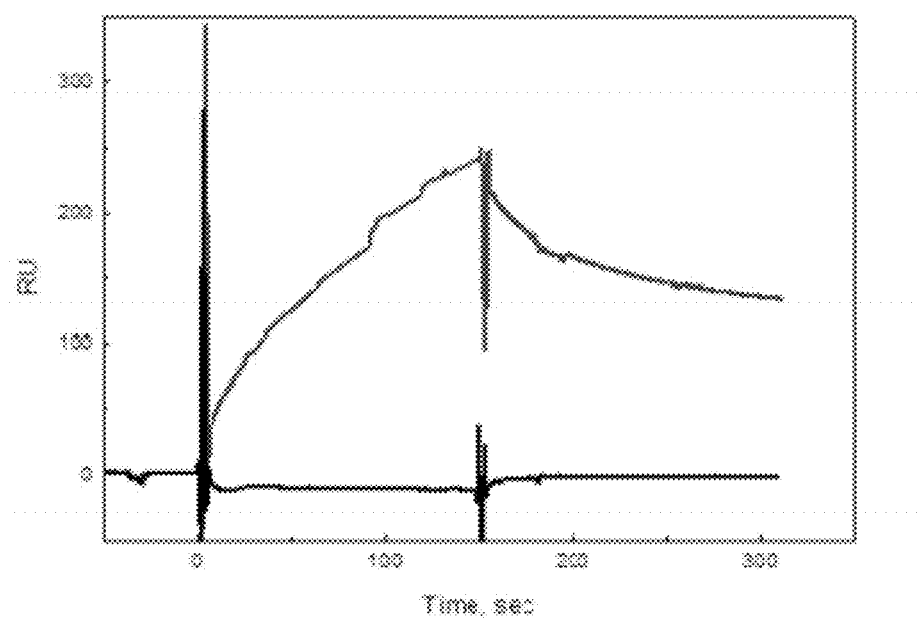

SEQUENCE LISTING

```
<160> NUMBER OF SEQ ID NOS: 9

<210> SEQ ID NO 1
<211> LENGTH: 295
<212> TYPE: PRT
<213> ORGANISM: Homo sapiens

<400> SEQUENCE: 1

Ser Pro Ile Met Asn Leu Glu Gln Ser Pro Leu Glu Glu Asp Met Ser
 1               5                  10                  15

Leu Phe Gly Asp Val Phe Ser Glu Gln Asp Gly Val Asp Phe Asn Thr
            20                  25                  30

Leu Leu Gln Ser Met Lys Asp Glu Phe Leu Lys Thr Leu Asn Leu Ser
        35                  40                  45

Asp Ile Pro Thr Gln Asp Ser Ala Lys Val Asp Pro Pro Glu Tyr Met
    50                  55                  60

Leu Glu Leu Tyr Asn Lys Phe Ala Thr Asp Arg Thr Ser Met Pro Ser
65                  70                  75                  80

Ala Asn Ile Ile Arg Ser Phe Lys Asn Glu Asp Leu Phe Ser Gln Pro
                85                  90                  95

Val Ser Phe Asn Gly Leu Arg Lys Tyr Pro Leu Leu Phe Asn Val Ser
            100                 105                 110

Ile Pro His His Glu Glu Val Ile Met Ala Glu Leu Arg Leu Tyr Thr
        115                 120                 125

Leu Val Gln Arg Asp Arg Met Ile Tyr Asp Gly Val Asp Arg Lys Ile
    130                 135                 140

Thr Ile Phe Glu Val Leu Glu Ser Lys Gly Asp Asn Glu Gly Glu Arg
145                 150                 155                 160

Asn Met Leu Val Leu Val Ser Gly Glu Ile Tyr Gly Thr Asn Ser Glu
                165                 170                 175

Trp Glu Thr Phe Asp Val Thr Asp Ala Ile Arg Arg Trp Gln Lys Ser
            180                 185                 190

Gly Ser Ser Thr His Gln Leu Glu Val His Ile Glu Ser Lys His Asp
        195                 200                 205

Glu Ala Glu Asp Ala Ser Ser Gly Arg Leu Glu Ile Asp Thr Ser Ala
    210                 215                 220

Gln Asn Lys His Asn Pro Leu Leu Ile Val Phe Ser Asp Asp Gln Ser
225                 230                 235                 240

Ser Asp Lys Glu Arg Lys Glu Glu Leu Asn Glu Met Ile Ser His Glu
                245                 250                 255

Gln Leu Pro Glu Leu Asp Asn Leu Gly Leu Asp Ser Phe Ser Ser Gly
            260                 265                 270

Pro Gly Glu Glu Ala Leu Leu Gln Met Arg Ser Asn Ile Ile Tyr Asp
        275                 280                 285

Ser Thr Ala Arg Ile Arg Arg
    290                 295

<210> SEQ ID NO 2
<211> LENGTH: 291
<212> TYPE: PRT
<213> ORGANISM: Mouse
```

```
<400> SEQUENCE: 2

Ser Pro Ile Met Gly Leu Glu Gln Ser Pro Leu Glu Glu Asp Met Pro
  1               5                  10                  15

Phe Phe Asp Asp Ile Phe Thr Glu Gln Asp Gly Ile Asp Phe Asn Thr
             20                  25                  30

Leu Leu Gln Ser Met Lys Asn Glu Phe Leu Lys Thr Leu Asn Leu Ser
         35                  40                  45

Asp Ile Pro Val Gln Asp Thr Gly Arg Val Asp Pro Pro Lys Tyr Met
 50                  55                  60

Leu Glu Leu Tyr Asn Lys Phe Ala Thr Asp Arg Thr Ser Met Pro Ser
 65                  70                  75                  80

Ala Asn Ile Ile Arg Ser Phe Lys Asn Glu Leu Phe Ser Gln Pro Val
                 85                  90                  95

Thr Phe Asn Gly Leu Arg Lys Tyr Pro Leu Leu Phe Asn Val Ser Ile
            100                 105                 110

Pro His His Glu Glu Val Val Met Ala Glu Leu Arg Leu Tyr Thr Leu
        115                 120                 125

Val Gln Arg Asp Arg Met Met Tyr Asp Gly Val Asp Arg Lys Ile Thr
    130                 135                 140

Ile Phe Glu Val Leu Glu Ser Ala Asp Gly Ser Glu Glu Glu Arg Ser
145                 150                 155                 160

Met Leu Val Leu Val Ser Thr Glu Ile Tyr Gly Thr Asn Ser Glu Trp
                165                 170                 175

Glu Thr Phe Asp Val Thr Asp Ala Thr Arg Arg Trp Gln Lys Ser Gly
            180                 185                 190

Pro Ser Thr His Gln Leu Glu Ile His Ile Glu Ser Arg Gln Asn Gln
        195                 200                 205

Ala Glu Asp Thr Gly Arg Gly Gln Leu Glu Ile Asp Met Ser Ala Gln
    210                 215                 220

Asn Lys His Asp Pro Leu Leu Val Val Phe Ser Asp Asp Gln Ser Asn
225                 230                 235                 240

Asp Lys Glu Gln Lys Glu Glu Leu Asn Glu Leu Ile Thr His Glu Gln
                245                 250                 255

Asp Leu Asp Leu Asp Ser Asp Ala Phe Phe Ser Gly Pro Asp Glu Glu
            260                 265                 270

Ala Leu Leu Gln Met Arg Ser Asn Met Ile Asp Asp Ser Ser Thr Arg
        275                 280                 285

Ile Arg Arg
    290

<210> SEQ ID NO 3
<211> LENGTH: 424
<212> TYPE: PRT
<213> ORGANISM: Homo sapiens

<400> SEQUENCE: 3

Met Gly Ser Leu Val Leu Thr Leu Cys Ala Leu Phe Cys Leu Ala Ala
  1               5                  10                  15

Tyr Leu Val Ser Gly Ser Pro Ile Met Asn Leu Glu Gln Ser Pro Leu
             20                  25                  30

Glu Glu Asp Met Ser Leu Phe Gly Asp Val Phe Ser Glu Gln Asp Gly
         35                  40                  45

Val Asp Phe Asn Thr Leu Leu Gln Ser Met Lys Asp Glu Phe Leu Lys
 50                  55                  60
```

```
Thr Leu Asn Leu Ser Asp Ile Pro Thr Gln Asp Ser Ala Lys Val Asp
 65                  70                  75                  80

Pro Pro Glu Tyr Met Leu Glu Leu Tyr Asn Lys Phe Ala Thr Asp Arg
                 85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 4
<211> LENGTH: 420
<212> TYPE: PRT
<213> ORGANISM: Mouse
```

<400> SEQUENCE: 4

```
Met Gly Ser Leu Val Leu Pro Leu Ser Ala Val Phe Cys Leu Val Ala
 1               5                  10                  15

His Ser Ala Ser Gly Ser Pro Ile Met Gly Leu Glu Gln Ser Pro Leu
            20                  25                  30

Glu Glu Asp Met Pro Phe Phe Asp Asp Ile Phe Thr Glu Gln Asp Gly
                35                  40                  45

Ile Asp Phe Asn Thr Leu Leu Gln Ser Met Lys Asn Glu Phe Leu Lys
 50                  55                  60

Thr Leu Asn Leu Ser Asp Ile Pro Val Gln Asp Thr Gly Arg Val Asp
 65                  70                  75                  80

Pro Pro Lys Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Leu
                100                 105                 110

Phe Ser Gln Pro Val Thr Phe Asn Gly Leu Arg Lys Tyr Pro Leu Leu
            115                 120                 125

Phe Asn Val Ser Ile Pro His His Glu Glu Val Val Met Ala Glu Leu
130                 135                 140

Arg Leu Tyr Thr Leu Val Gln Arg Asp Arg Met Met Tyr Asp Gly Val
145                 150                 155                 160

Asp Arg Lys Ile Thr Ile Phe Glu Val Leu Ser Ala Asp Gly Ser
                165                 170                 175

Glu Glu Glu Arg Ser Met Leu Val Leu Val Ser Thr Glu Ile Tyr Gly
                180                 185                 190

Thr Asn Ser Glu Trp Glu Thr Phe Asp Val Thr Asp Ala Thr Arg Arg
            195                 200                 205

Trp Gln Lys Ser Gly Pro Ser Thr His Gln Leu Glu Ile His Ile Glu
210                 215                 220

Ser Arg Gln Asn Gln Ala Glu Asp Thr Gly Arg Gly Gln Leu Glu Ile
225                 230                 235                 240

Asp Met Ser Ala Gln Asn Lys His Asp Pro Leu Leu Val Val Phe Ser
                245                 250                 255

Asp Asp Gln Ser Asn Asp Lys Glu Gln Lys Glu Glu Leu Asn Glu Leu
                260                 265                 270

Ile Thr His Glu Gln Asp Leu Asp Leu Asp Ser Asp Ala Phe Phe Ser
            275                 280                 285

Gly Pro Asp Glu Glu Ala Leu Leu Gln Met Arg Ser Asn Met Ile Asp
290                 295                 300

Asp Ser Ser Thr Arg Ile Arg Arg Asn Ala Lys Gly Asn Tyr Cys Lys
305                 310                 315                 320

Lys Thr Pro Leu Tyr Ile Asp Phe Lys Glu Ile Gly Trp Asp Ser Trp
                325                 330                 335

Ile Ile Ala Pro Pro Gly Tyr Glu Ala Tyr Glu Cys Arg Gly Val Cys
            340                 345                 350

Asn Tyr Pro Leu Ala Glu His Leu Thr Pro Thr Lys His Ala Ile Ile
                355                 360                 365

Gln Ala Leu Val His Leu Lys Asn Ser Gln Lys Ala Ser Lys Ala Cys
370                 375                 380

Cys Val Pro Thr Lys Leu Asp Pro Ile Ser Ile Leu Tyr Leu Asp Lys
385                 390                 395                 400
```

Gly Val Val Thr Tyr Lys Phe Lys Tyr Glu Gly Met Ala Val Ser Glu
                405                 410                 415

Cys Gly Cys Arg
            420

<210> SEQ ID NO 5
<211> LENGTH: 885
<212> TYPE: DNA
<213> ORGANISM: Homo sapiens

<400> SEQUENCE: 5
agccccatca tgaacctaga gcagtctcct ctggaagaag atatgtccct ctttggtgat      60
gttttctcag agcaagacgg tgtcgacttt aacacactgc tccagagcat gaaggatgag     120
tttcttaaga cactaaacct ctctgacatc cccacgcagg attcagccaa ggtggaccca     180
ccagagtaca tgttggaact ctacaacaaa tttgcaacag atcggacctc catgccctct     240
gccaacatca ttaggagttt caagaatgaa gatctgtttt cccagccggt cagttttaat     300
gggctccgaa ataccccct cctcttcaat gtgtccattc ctcaccatga gaggtcatc      360 atggctgaac ttaggctata cacactggtg caaagggatc gtatgatata cgatggagta     420
gaccggaaaa ttaccatttt tgaagtgctg agagcaaag gggataatga gggagaaaga     480
aacatgctgg tcttggtgtc tggggagata tatggaacca acagtgagtg ggagactttt     540
gatgtcacag atgccatcag acgttggcaa aagtcaggct catccaccca ccagctggag     600
gtccacattg agagcaaaca cgatgaagct gaggatgcca gcagtggacg gctagaaata     660
gataccagtg cccagaataa gcataaccct tgctcatcg tgttttctga tgaccaaagc      720
agtgacaagg agaggaagga ggaactgaat gaaatgattt cccatgagca acttccagag     780
ctggacaact gggcctgga tagcttttcc agtggacctg ggaagaggc tttgttgcag       840 atgagatcaa acatcatcta tgactccact gcccgaatca gaagg                     885

<210> SEQ ID NO 6
<211> LENGTH: 873
<212> TYPE: DNA
<213> ORGANISM: Mouse

<400> SEQUENCE: 6
agccccatta tgggcccttga gcagtcgccc ctggaagaag acatgccctt ctttgatgat      60
atcttcacgg agcaagatgg tattgacttc aacacactgc tgcagagcat gaagaacgag     120
tttctcaaga cgctgaactt gtcggacatt cctgtgcagg acacgggcag agtggatcca     180
ccaaagtaca tgctggagct ctacaacaaa ttcgccacag accggacctc catgccgtct     240
gctaacatca tccggagctt caagaacgaa ctgttttctc aaccagtcac ttttaatggg     300
ctccggaaat atcctctcct cttcaatgtg tctatccctc accatgaaga ggtcgtcatg     360
gctgaactgc ggttgtacac gctggtgcag agagatcgca tgatgtatga tggcgtggac     420
cgtaaaatta ccattttga ggtactagag agtgcagacg gtagcgagga ggagaggagc      480
atgctggtct tagtatcaac agagatctac ggaaccaaca gtgagtggga gacatttgac     540
gtcacagatg ccaccagacg ttggcaaaag tcaggcccat caacccatca gctggagatc     600
cacatagaaa gcagacaaaa ccaagctgag gacaccggaa ggggacaact ggaaatagat     660
atgagtgccc aaaataagca tgaccctttg ctggttgtgt tttctgatga ccaaagcaat     720
gacaaggagc agaaagaaga actgaacgaa ttgatcaccc atgagcagga tctggacctg     780

| | |
|---|---|
| gactcagatg ctttcttcag tgggcccgat gaagaggctc tgctgcagat gaggtcgaac | 840 |
| atgattgatg attcgtccac tcggatcagg agg | 873 |

<210> SEQ ID NO 7
<211> LENGTH: 1272
<212> TYPE: DNA
<213> ORGANISM: Homo sapiens

<400> SEQUENCE: 7

| | |
|---|---|
| atgggctctc tggtcctgac actgtgcgct ctttctctgcc tggcagctta cttggttct | 60 |
| ggcagcccca tcatgaacct agagcagtct cctctggaag aagatatgtc cctctttggt | 120 |
| gatgttttct cagagcaaga cggtgtcgac tttaacacac tgctccagag catgaaggat | 180 |
| gagtttctta agacactaaa cctctctgac atccccacgc aggattcagc caaggtggac | 240 |
| ccaccagagt acatgttgga actctacaac aaatttgcaa cagatcggac ctccatgccc | 300 |
| tctgccaaca tcattaggag tttcaagaat gaagatctgt tttcccagcc ggtcagtttt | 360 |
| aatgggctcc gaaaataccc cctcctcttc aatgtgtcca ttcctcacca tgaagaggtc | 420 |
| atcatggctg aacttaggct atacacactg gtgcaaaggg atcgtatgat atacgatgga | 480 |
| gtagaccgga aaattaccat ttttgaagtg ctggagagca aggggataat tgagggagaa | 540 |
| agaaacatgc tggtcttggt gtctggggag atatatggaa ccaacagtga gtgggagact | 600 |
| tttgatgtca cagatgccat cagacgttgg caaaagtcag gctcatccac ccaccagctg | 660 |
| gaggtccaca ttgagagcaa acacgatgaa gctgaggatg ccagcagtgg acggctagaa | 720 |
| atagatacca gtgcccagaa taagcataac cctttgctca tcgtgttttc tgatgaccaa | 780 |
| agcagtgaca aggagaggaa ggaggaactg aatgaaatga tttcccatga gcaacttcca | 840 |
| gagctggaca acttgggcct ggatagcttt tccagtggac ctgggggaaga ggctttgttg | 900 |
| cagatgagat caaacatcat ctatgactcc actgcccgaa tcagaaggaa cgccaaagga | 960 |
| aactactgta gaggaccccc gctctacatc gacttcaagg agattgggtg ggactcctgg | 1020 |
| atcatcgctc cgcctggata cgaagcctat gaatgccgtg tgtttgtaa ctacccctg | 1080 |
| gcagagcatc tcacacccac aaagcatgca attatccagg ccttggtcca cctcaagaat | 1140 |
| tcccagaaag cttccaaagc ctgctgtgtg cccacaaagc tagagcccat ctccatcctc | 1200 |
| tatttagaca aaggcgtcgt cacctacaag tttaaatacg aaggcatggc cgtctccgaa | 1260 |
| tgtggctgta ga | 1272 |

<210> SEQ ID NO 8
<211> LENGTH: 1260
<212> TYPE: DNA
<213> ORGANISM: Mouse

<400> SEQUENCE: 8

| | |
|---|---|
| atggggtctc tggttctgcc gctgagcgcc gtcttctgcc tggtggctca ctcggcttct | 60 |
| ggcagcccca ttatgggcct tgagcagtcg cccctggaag aagacatgcc cttctttgat | 120 |
| gatatcttca cggagcaaga tggtattgac ttcaacacac tgctgcagag catgaagaac | 180 |
| gagtttctca agacgctgaa cttgtcgac attcctgtgc aggacacggg cagagtggat | 240 |
| ccaccaaagt acatgctgga gctctacaac aaattcgcca cagaccggac ctccatgccg | 300 |
| tctgctaaca tcatccggag cttcaagaac gaactgtttt ctcaaccagt cacttttaat | 360 |
| gggctccgga aatatcctct cctcttcaat gtgtctatcc ctcaccatga gaggtcgtc | 420 |
| atggctgaac tgcggttgta cacgctggtg cagagagatc gcatgatgta tgatggcgtg | 480 |

```
gaccgtaaaa ttaccatttt tgaggtacta gagagtgcag acggtagcga ggaggagagg      540
agcatgctgg tcttagtatc aacagagatc tacggaacca acagtgagtg ggagacattt      600
gacgtcacag atgccaccag acgttggcaa aagtcaggcc catcaaccca tcagctggag      660
atccacatag aaagcagaca aaaccaagct gaggacaccg gaaggggaca actggaaata      720
gatatgagtg cccaaaataa gcatgaccct ttgctggttg tgttttctga tgaccaaagc      780
aatgacaagg agcagaaaga gaactgaac gaattgatca cccatgagca ggatctggac       840
ctggactcag atgctttctt cagtgggccc gatgaagagg ctctgctgca gatgaggtcg      900
aacatgattg atgattcgtc cactcggatc aggaggaacg ccaagggaa ctactgtaag        960 aagaccccac tatacatcga cttcaaggag attgggtggg actcctggat catcgctcct     1020
cctgggtatg aagcctatga gtgccggggt gtgtgtaact accctctggc ggagcacctc     1080
acacctacaa aacacgcaat tattcaggcc ttggtccacc tcaagaattc ccagaaagct     1140
tccaaagcct gctgtgtgcc cacgaagctg gatcccatct ccatcctcta tttagataaa     1200
ggtgtcgtca cctacaagtt taaatatgaa gggatggctg tgtctgagtg tggctgtaga     1260
```

<210> SEQ ID NO 9
<211> LENGTH: 225
<212> TYPE: PRT
<213> ORGANISM: Homo sapiens
<220> FEATURE:
<221> NAME/KEY: VARIANT
<222> LOCATION: 43
<223> OTHER INFORMATION: Xaa = Asp or Ala
<221> NAME/KEY: VARIANT
<222> LOCATION: 100
<223> OTHER INFORMATION: Xaa = Lys or Ala
<221> NAME/KEY: VARIANT
<222> LOCATION: 212
<223> OTHER INFORMATION: Xaa = Asn or Ala

<400> SEQUENCE: 9

```
Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Xaa Val Ser His Glu Asp
         35                  40                  45

Pro Glu Val Lys Phe Asn Trp Tyr Val Asp Gly Val Glu Val His Asn
     50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190
```

```
Ser Arg Trp Gln Gln Gly Asn Val Phe Ser Cys Ser Val Met His Glu
    195                 200                 205

Ala Leu His Xaa His Tyr Thr Gln Lys Ser Leu Ser Pro Gly
    210                 215                 220

Lys
225
```

BMP10 PROPEPTIDES AND RELATED METHODS

RELATED APPLICATIONS

This application is a continuation of U.S. application Ser. No. 12/316,083, filed Dec. 9, 2008, now U.S. Pat. No. 8,287,868, which is a continuation of U.S. application Ser. No. 11/128,937 filed May 12, 2005, now U.S. Pat. No. 7,741,284, which claims the benefit of the filing date of U.S. Provisional Application No. 60/570,779, filed May 12, 2004. The specifications of each of the foregoing applications are incorporated by reference herein in their entirety.

SEQUENCE LISTING

The instant application contains a Sequence Listing which has been submitted via EFS-Web and is hereby incorporated by reference in its entirety. Said ASCII copy, created on Apr. 6, 2012, is named PHPH-P03-007Seq.txt and is 19,878 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Many of members of the superfamily perform important functions during embryonic development in pattern formation and tissue specification and can influence a variety of differentiation processes, including adipogenesis, myogenesis, chondrogenesis, cardiogenesis, hematopoiesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF-8/myostatin gene that causes a marked increase in muscle mass. Grobet et al., Nat. Genet. 1997 September; 17(1):71-4. Changes in fat, bone, cartilage, muscle and other tissues may be achieved by agonizing or antagonizing signaling that is mediated by an appropriate TGF-beta family member. Thus, there is a need for agents (e.g., polypeptides) that function as potent regulators of TGF-beta signaling.

SUMMARY OF THE INVENTION

In certain aspects, the present disclosure provides BMP10 propeptides. Such propeptides may be used for the treatment of heart disorders, and particularly for the treatment of heart disorders that are correlated with an undesirable growth and/or proliferation of cardiomyocytes. For example various cardiomyopathies and congenital heart diseases may be treated with a BMP10 propeptide. BMP10 propeptides may also be used to antagonize BMP10 generally, in any BMP10 related process. BMP10 propeptides may antagonize other members of the BMP family and may therefore be useful in the treatment of additional disorders. Examples of BMP10 propeptides include the naturally occurring propeptides of BMP10, as well as functional variants thereof. Additionally, the disclosure provides antibodies that bind a mature BMP10 peptide in a manner similar to a BMP10 propeptide. Such antibodies may also be used to treat heart disorders or other BMP10 related disorders.

In certain aspects, the disclosure provides pharmaceutical preparations for treating heart disorders. Such preparations may comprise a BMP10 propeptide that binds to a mature BMP10 polypeptide and a pharmaceutically acceptable carrier. Optionally the BMP10 propeptide binds to a mature BMP10 with a Kd less than 10 micromolar or less than 1 micromolar, 100, 10 or 1 nanomolar. Optionally, the BMP10 propeptide inhibits an activity of mature BMP10, such as receptor binding or intracellular signal transduction events triggered by BMP10. A BMP10 propeptide for use in such a preparation may be any of those disclosed herein, such as a polypeptide having an amino acid sequence of SEQ ID NO:1 or 2 or having an amino acid sequence that is at least 80%, 85%, 90%, 95%, 97% or 99% identical to an amino acid sequence of SEQ ID NO:1 or 2. A BMP10 propeptide may include a functional fragment of a natural BMP10 propeptide, such as one comprising at least 10, 20 or 30 amino acids of SEQ ID NO:1 or 2. A BMP10 propeptide will generally not contain a full-length or functional portion of a mature BMP10 polypeptide, and preferably a BMP10 propeptide will include no more than 50, 40, 30, 20, 10 or 5 amino acids of a mature portion of a BMP10 polypeptide. A BMP10 propeptide may include one or more alterations in the amino acid sequence relative to a naturally occurring BMP10 propeptide. The alteration in the amino acid sequence may, for example, alter glycosylation of the polypeptide when produced in a mammalian, insect or other eukaryotic cell or alter proteolytic cleavage of the polypeptide relative to the naturally occurring BMP10 polypeptide. A BMP10 propeptide may be a fusion protein that has, as one domain, a BMP10 propeptide (including any of the various truncations or variations described herein) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A BMP10 propeptide fusion protein may include an immunoglobulin Fc domain or a serum albumin. A fusion protein may include a purification subsequence, such as an epitope tag, a FLAG tag, a polyhistidine sequence, and a GST fusion. Optionally, a BMP10 propeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a heart disorder. Examples of compounds that are used to treat heart disorders include: beta blockers, anti-hypertensives, cardiotonics, anti-thrombotics, vasodilators, hormone antagonists, endothelin antagonists, calcium channel blockers, phosphodiesterase inhibitors, angiotensin type 2 antagonists and cytokine blockers/inhibitors. Preferably, a pharmaceutical preparation is substantially pyrogen free. Preferably, a pharmaceutical composition comprising a BMP10 propeptide will not include, as a separate component, an active mature BMP10 protein.

In certain aspects, the disclosure provides packaged pharmaceuticals comprising a pharmaceutical preparation described herein and labeled for use in treating a heart disorder. Optionally, the packaged pharmaceutical is labeled for use in treating a cardiomyopathy, such as a dilated cardiomyopathy, a hypertrophic cardiomyopathy, a restrictive cardiomyopathy or a congenital heart disease. In a preferred embodiment, the packaged pharmaceutical is labeled for use in treating a congenital heart disease that results in a progressive cardiomyopathy. Examples of such congenital heart disorders include those associated with a dominant negative Nkx2-5 allele.

In certain aspects, the disclosure provides nucleic acids encoding a BMP10 propeptide that do not encode a complete, translatable mature portion of a BMP10. An isolated polynucleotide may comprise a coding sequence for a BMP10 propeptide, such as described above. An isolated nucleic acid may include a sequence coding for a BMP10 propeptide and a sequence that would code for part or all of a mature portion, but for a stop codon positioned within the mature portion or positioned between the propeptide and the mature portion. For example, an isolated polynucleotide may comprise a full-length BMP10 polynucleotide sequence such as SEQ ID NO:7 or 8, or a partially truncated version, said isolated polynucleotide further comprising a transcription termination codon at least three hundred nucleotides before the 3'-terminus or otherwise positioned such that translation of the polynucleotide gives rise to a BMP10 propeptide optionally fused to a truncated mature peptide portion. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a BMP10 propeptide. Such a method may include expressing any of the propeptide encoding nucleic acids disclosed herein in a suitable cell, such as a Chinese hamster ovary (CHO) cell. Such a method may comprise: a) culturing a cell under conditions suitable for expression of the propeptide, wherein said cell is transformed with a BMP10 propeptide expression construct; and b) recovering the propeptide so expressed. Propeptides may be recovered as crude, partially purified or highly purified fractions using any of the well known techniques for obtaining protein from cell cultures.

In certain aspects, the disclosure provides methods for inhibiting cardiomyocyte growth, in vivo or ex vivo. A method for inhibiting cardiomyocyte growth may comprise contacting a cardiomyocyte with an effective amount of a BMP10 propeptide disclosed herein. Optionally, the cardiomyocyte is a mammalian cardiomyocyte, such as a human cardiomyocyte. Examples of cardiomyocytes include pacemaker cells (e.g. from the sinoatrial node or the atrioventricular node), His bundle (HIS) cells, Purkinje fiber (PUR) cells, atrial working myocytes, and ventricular working myocytes.

In certain aspects, a BMP10 polypeptide disclosed herein may be used in a method for treating a subject having a disorder associated with abnormal cell growth and differentiation. A method may comprise administering to a subject in need thereof an effective amount of a BMP10 propeptide.

In certain aspects, the disclosure provides methods for antagonizing a BMP10 activity in a mammal or in a cell, ex vivo or in vivo. A method may comprise administering to the mammal or contacting the cell with a BMP10 propeptide. The effect of a BMP10 propeptide on BMP10 signaling may be monitored by detecting a signal transduction event mediated by mature BMP10. The effect of a BMP10 propeptide on mature BMP10 activity may also be monitored by detecting the degree of cell proliferation of BMP10-sensitive cell type. Optionally, a cell to be contacted is a mammalian cell, such as a human cell, and preferably a cardiomyocyte or a cardiomyocyte precursor cell.

In certain aspects, the disclosure provides a use of a BMP10 propeptide for making a medicament for the treatment of a heart disorder. Preferred heart disorders include dilated cardiomyopathy, hypertrophic cardiomyopathy, restrictive cardiomyopathy and congenital heart diseases, particularly those congenital heart diseases that result in progressive cardiomyopathy or are associated with a mutation in the Nkx2-5 gene, particularly dominant negative Nkx2-5 alleles.

In certain aspects, a BMP10 propeptide is expected to have an effect on bone, cartilage and skeletal muscle tissue, either through an effect on BMP10 or through a BMP10 independent effect. Accordingly, a BMP10 propeptide may be administered to a subject suffering from a disorder related to bone, cartilage or skeletal muscle.

In further aspects, the disclosure provides methods for identifying an agent that may be used for treating a heart disorder. A method may comprise: a) identifying a test agent that binds a mature BMP10 polypeptide competitively with a BMP10 propeptide; and b) evaluating the effect of the agent on a heart disorder. A test agent may be, for example, a variant BMP10 propeptide, an antibody, or a small molecule. In further aspects, the disclosure provides methods for identifying an agent that modulates cardiomyocyte proliferation. A method may comprise (a) identifying a test agent that binds a mature portion of BMP10 competitively with a BMP10 propeptide; and (b) evaluating the effect of the agent on cardiomyocyte proliferation.

BRIEF DESCRIPTION OF THE DRAWINGS

FIG. 1 shows a human BMP10 propeptide amino acid sequence (SEQ ID NO: 1).

FIG. 2 shows a mouse BMP10 propeptide amino acid sequence (SEQ ID NO: 2).

FIG. 3 shows a human BMP10 precursor amino acid sequence (SEQ ID NO: 3). The signal peptide (residues 1-21) is underlined; the prodomain (residues 22-316) is in bold, also referred to as SEQ ID NO: 1; and the mature protein (residues 317-424) is shaded. The potential N-linked glycosylation sites are boxed.

FIG. 4 shows a mouse BMP10 precursor amino acid sequence (SEQ ID NO: 4). The signal peptide (residues 1-21) is underlined; the prodomain (residues 22-312) is in bold, also referred to as SEQ ID NO: 2; and the mature protein (residues 313-420) is shaded. The potential N-linked glycosylation sites are boxed.

FIG. 5 shows a nucleic acid sequence encoding a human BMP10 propeptide, designed as SEQ ID NO: 5.

FIG. 6 shows a nucleic acid sequence encoding a mouse BMP10 propeptide, designed as SEQ ID NO: 6.

FIG. 7 shows a nucleic acid sequence encoding a human BMP10 precursor protein, designed as SEQ ID NO: 7.

FIG. 8 shows a nucleic acid sequence encoding a mouse BMP10 precursor protein, designed as SEQ ID NO: 8.

FIG. 9 shows human Fc amino acid sequence. Certain useful mutations are shown in bold.

FIG. 10 shows that mature BMP-10 binds to BMP-10 propeptide. A BiaCore™ chip was prepared with immobilized BMP-10 propeptide. The chip was exposed to conditioned media from cells expressing (upper curve) or not expressing (lower curve) BMP10. Significant binding activity was observed in the conditioned media from cells expressing BMP-10, indicating that BMP-10 propeptide does bind to the mature portion.

DETAILED DESCRIPTION OF THE INVENTION

1. Overview

The present invention relates to Bone morphogenetic protein-10 (BMP10) propeptides. As used herein, the term "BMP10 polypeptide" refers to the family of bone morphogenetic proteins of the type 10, derived from any species. The term "BMP10 polypeptide" includes any of the naturally occurring BMP10 polypeptides as well as polypeptides derived from the sequence of any naturally occurring BMP10 whose mature sequence is at least about 75% homologous with the sequence of a mature BMP10, and preferably at least 80%, 85%, 90%, 95%, 97%, 99% or greater homology. Members of the BMP10 family are generally encoded as a larger precursor, and members of the family share a region of high homology near the C-terminus, corresponding generally to the mature portion. For example, human BMP10 mature peptide shares about 80% amino acid identity with mouse BMP10 in the mature peptide (mature domain).

A naturally occurring BMP10 protein is generally encoded as a larger precursor that typically contains a signal sequence at its N-terminus followed by a dibasic amino acid cleavage site and a propeptide, followed by another dibasic amino acid cleavage site and a mature domain. Thus a propeptide or prodomain is the portion that is N-terminal to the mature domain and C-terminal to the signal peptide. Optionally, a BMP10 propeptide, after cleavage, reassociates with its mature peptide covalently or non-covalently, as in the case of insulin, relaxin, inhibin, activin, and TGF-β. The term "BMP10 propeptide" is used to refer to polypeptides comprising any naturally occurring propeptide of a BMP-10 family member as well as any variants thereof (including mutants, fragments and peptidomimetic forms) that retain a useful activity. Examples of useful activities include binding to the mature portion of a BMP10 and acting as an antagonist of an activity of a mature BMP10. As the term is used herein, BMP10 propeptides include fragments, functional variants, and modified forms (e.g., peptidomimetic forms) of BMP10 propeptides. A "BMP10 propeptide" will not include a full-length mature BMP10 domain, although a BMP10 propeptide may include portions of the mature domain, particularly portions that are not fully functional. For example, a BMP10 propeptide may contain fewer than 50, 40, 30, 20, 10 or 5 amino acids of its cognate mature domain. Functional variants of a BMP-10 propeptide may be characterized by, for example, binding to mature BMP-10 protein and/or the ability to competitively inhibit the binding of BMP-10 to a type II receptor such as ActRIIA.

Examples of BMP10 precursor proteins include human BMP10 and mouse BMP10, whose precursor sequences including signal peptide, propeptide, and mature peptide, are illustrated in FIGS. 3 and 4, respectively.

Recently, BMP10 proteins are found to regulate cardiac morphogenesis and myocardial trabecular formation. Neuhaus et al., 1999, Mech. Dev. 80:181-184. BMP10 is overexpressed in the heart muscle of humans and mice having a congenital heart disorder caused by a mutation in Nkx2-5, and is implicated as a causative agent in various cardiomyopathies. Pashmforoush et al., 2004, Cell 117:373-386. Others have suggested a role for BMP10 in bone and cartilage development, and other processes characteristic of the BMP family as a whole. See, e.g., U.S. Pat. No. 5,637,480. Accordingly, a BMP10 propeptide disclosed herein may be used to treat a variety of disorders, including heart disorders and other disorders related to undesirable BMP10 activity or undesirable activity of another member of the BMP10 family which the BMP10 propeptide antagonizes.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The disclosure may refer to the comparison of sequences to each other, including wild-type sequence to one or more mutants/sequence variants. Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. BMP10 Propeptides

In certain aspects, the invention relates to BMP10 propeptides. Preferably, these fragments, functional variants, and modified forms have biological activities that are similar to or the same as their corresponding wild-type BMP10 propeptides. For example, a BMP10 propeptide of the invention may inhibit function of a BMP10 mature protein, for example, by binding to the BMP10 mature protein. Optionally, a BMP10 propeptide inhibits or decreases growth of cardiac tissues and cells. Examples of BMP10 propeptides include a human BMP10 propeptide (SEQ ID NO: 1) and a mouse BMP10 propeptide (SEQ ID NO: 2).

In one specific example, human BMP10 cDNA (SEQ ID NO: 7, FIG. 7) encodes a 424-amino acid precursor protein (SEQ ID NO: 3, FIG. 3). Cleavage of the human BMP10 precursor protein at a putative polybasic proteolytic cleavage site (residues 313-316 of SEQ ID NO: 3) generates a mature BMP10 protein consisting of 108 amino acids (FIG. 3) and a BMP10 propeptide consisting of 295 amino acids (FIGS. 1 and 3; SEQ ID NO: 1). The human BMP10 propeptide contains potential glycosylation sites (FIG. 3).

In another specific example, mouse BMP10 cDNA (SEQ ID NO: 8, FIG. 8) encodes a 420-amino acid precursor protein (SEQ ID NO: 4, FIG. 4). Cleavage of the mouse BMP10 precursor protein at a putative polybasic proteolytic cleavage site (residues 309-312 of SEQ ID NO: 4) generates a mouse mature BMP10 protein consisting of 108 amino acids and a BMP10 propeptide consisting of 291 amino acids (FIGS. 2 and 4; SEQ ID NO: 2). The mouse BMP10 propeptide contains potential glycosylation sites (FIG. 4).

In certain embodiments, isolated fragments of the BMP10 propeptides can be obtained by screening polypeptides recombinantly produced from the corresponding fragment of the nucleic acid encoding a BMP10 propeptide (e.g., SEQ ID NO: 1 or 2). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of BMP10 activity.

In certain embodiments, a functional variant of the BMP10 propeptides has an amino acid sequence that is at least 75% identical to an amino acid sequence as set forth in SEQ ID NO: 1 or 2. In certain cases, the functional variant has an amino acid sequence at least 80%, 85%, 90%, 95%, 97%, 98%, 99% or 100% identical to an amino acid sequence as set forth in SEQ ID NO: 1 or 2. Preferably such variants retain the ability to bind to BMP10.

In certain embodiments, the present invention contemplates making functional variants by modifying the structure of a BMP10 propeptide for such purposes as enhancing therapeutic efficacy, or stability (e.g., ex vivo shelf life and resistance to proteolytic degradation in vivo). Such modified BMP10 propeptides when designed to retain at least one activity of the naturally-occurring form of the BMP10 propeptides, are considered functional equivalents of the naturally-occurring propeptides. Modified BMP10 propeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a BMP10 propeptide results in a functional homolog can be readily determined by assessing the ability of the variant propeptide to produce a response in cells in a fashion similar to the wild-type propeptide.

In certain embodiments, the present invention contemplates making mutations in the proteolytic cleavage site of the BMP10 sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the BMP10 propeptide sequences so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type BMP10 propeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a BMP10 propeptide is by chemical or enzymatic coupling of glycosides to the BMP10 propeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a BMP10 propeptide may be accomplished chemically and/or enzymatically. Chemical deglycosylation may involve, for example, exposure of the BMP10 propeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on BMP10 propeptides can be achieved by the use of a variety of endo- and exo-glycosidases as described by Thotakura et al. (1987) Meth. Enzymol. 138: 350. The sequence of a propeptide may be adjusted, as appropriate, depending on the type of expression system used, as mammalian, yeast, insect and plant cells may all introduce differing glycosylation patterns that can be affected by the amino acid sequence of the peptide.

This disclosure further contemplates a method of generating mutants, particularly sets of combinatorial mutants of the BMP10 propeptide, as well as truncation mutants; pools of combinatorial mutants are especially useful for identifying functional variant sequences. The purpose of screening such combinatorial libraries may be to generate, for example, BMP10 propeptide variants which can act as either agonists or antagonist, or alternatively, which possess novel activities all together. A variety of screening assays are provided below, and such assays may be used to evaluate variants. For example, a BMP10 propeptide variant may be screened for ability to bind to a BMP10 mature polypeptide or for the ability to prevent binding of a BMP10 mature polypeptide to a cell expressing a BMP10 receptor.

The activity of a BMP10 propeptide or its variants may also be tested in a cell-based or in vivo assay. For example, the effect of a BMP10 propeptide variant on proliferative activity in cardiomyocytes may be assessed. As another example, the effect of a BMP10 propeptide variant on gene expression of a cardiogenic factor (e.g., NKX2.5 and MEF2C) may be assessed. In certain cases, such assays are performed in cells or tissues isolated from the developing heart. This may, as needed, be performed in the presence of recombinant BMP10, and cells may be transfected so as to produce BMP10, and the subject BMP10 propeptide variant. Likewise, a BMP10 propeptide may be administered to a mouse or other animal, and cardiac growth may be assessed, for example, by measuring the thickening of the innermost layer of the walls (e.g., the formation of myocardial ridges or trabeculae).

Combinatorially-derived variants can be generated which have a selective potency relative to a naturally occurring BMP10 propeptide. Such variant proteins, when expressed from recombinant DNA constructs, can be used in gene therapy protocols. Likewise, mutagenesis can give rise to variants which have intracellular half-lives dramatically different than the corresponding wild-type propeptide. For example, the altered protein can be rendered either more stable or less stable to proteolytic degradation or other cellular process which result in destruction of, or otherwise inactivation of a native BMP10 propeptide. Such variants, and the genes which encode them, can be utilized to alter BMP10 propeptide levels by modulating the half-life of the propeptide. For instance, a short half-life can give rise to more transient biological effects and, when part of an inducible expression system or scheduled dosing regimen, can allow tighter control of recombinant BMP10 propeptide levels in the treated subject.

In a preferred embodiment, the combinatorial library is produced by way of a degenerate library of genes encoding a library of polypeptides which each include at least a portion of potential BMP10 propeptide sequences. For instance, a mixture of synthetic oligonucleotides can be enzymatically ligated into gene sequences such that the degenerate set of potential BMP10 propeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, BMP10 propeptide variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218: 597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of BMP10 propeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of BMP10 propeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the BMP10 propeptides of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the BMP10 propeptides.

To illustrate, by employing scanning mutagenesis to map the amino acid residues of a BMP10 propeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the BMP10 propeptides of the invention may further comprise post-translational modifications in addition to any that are naturally present in the propeptide. Such modifications include, but are not limited to, acetylation, carboxylation, PEGylation, glycosylation, phosphorylation, lipidation, and acylation. As a result, the modified BMP10 propeptides may contain non-amino acid elements, such as polyethylene glycols, lipids, poly- or monosaccharide, and phosphates. Effects of such non-amino acid elements on the functionality of a BMP10 propeptide may be tested as described herein for other BMP10 propeptide variants. When a BMP10 propeptide is produced in cells by cleaving a nascent form of the BMP10 protein, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the BMP10 protein into a BMP10 propeptide.

In certain aspects, functional variants or modified forms of the BMP10 propeptides include fusion proteins having at least a portion of the BMP10 propeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the BMP10 propeptide. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a BMP10 propeptide is fused with a domain that stabilizes the propeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. In addition, Fc fusions tend to dimerize, providing a dimeric BMP-10 propeptide. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

It is understood that different elements of the fusion proteins may be arranged in any manner that is consistent with the desired functionality. For example, a BMP10 propeptide may be placed C-terminal to a heterologous domain, or, alternatively, a heterologous domain may be placed C-terminal to a BMP10 propeptide. The propeptide domain and the heterologous domain need not be adjacent in a fusion protein, and additional domains or amino acid sequences may be included C- or N-terminal to either domain or between the domains.

In certain embodiments, the BMP10 propeptides of the present invention contain one or more modifications that are capable of stabilizing the BMP10 propeptides. For example, such modifications enhance the in vitro half life of the propeptides, enhance circulatory half life of the propeptides or reducing proteolytic degradation of the propeptides. Such stabilizing modifications include, but are not limited to, fusion proteins (including, for example, fusion proteins comprising a BMP10 propeptide and a stabilizer domain), modifications of a glycosylation site (including, for example, addition of a glycosylation site to a BMP10 propeptide), and modifications of carbohydrate moiety (including, for example, removal of carbohydrate moieties from a BMP10 propeptide). In the case of fusion proteins, a BMP10 propeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol (PEG). PEG may be affixed to BMP-10 propeptides in a variety of sizes, ranging from 1000 D to 50,000 D or more molecular weight polymers and may be branched or unbranched. PEG polymers may be affixed to propeptides in a selective, residue specific manner, particularly when directed against the N-terminal amine or an engineered cysteine. PEG polymers may also be affixed in a relatively uncontrolled reaction, in which primary amines and/or sulfhydryl groups may be reacted. The stoichiometry may range from 1:1 (PEG:Propeptide) to 2:1 and higher.

In certain embodiments, the BMP-10 propeptide is fused with an immunoglobulin Fc domain. In a preferred embodiment, the Fc domain is an IgG1 Fc fragment. An IgG1 Fc fragment may include various alterations, including, for example, mutations that reduce binding to Fcγ Receptor and mutations that decreased binding to MHC class I-related Fc-receptor (FcRN). Examples of mutations include mutations in the an Fc portion at positions 265 (Asp to Ala), 322 (Lys to Ala), and 434 (Asn to Ala). An example of an Fc sequence is shown in FIG. 9.

In certain embodiments, a BMP-10 propeptide may be fused or otherwise complexed with an agent that antagonizes the Type I receptor binding function of BMP-10. Such an agent may be, for example, an antibody that binds the Type I binding site and competes with a cognate Type I receptor. An agent may also be, for example, a soluble portion of a Type I receptor. A Type I receptor may be, for example, any of the activin receptor like kinases (ALKs), e.g., ALK1-7.

In certain embodiments, the present invention makes available isolated and/or purified forms of the BMP10 propeptides, which are isolated from, or otherwise substantially free of, other proteins.

In certain embodiments, BMP10 propeptides (unmodified or modified) of the invention can be produced by a variety of art-known techniques. For example, such BMP10 propeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the BMP10 propeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified BMP10 propeptides may be produced by digestion of naturally occurring or recombinantly produced BMP10 by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such BMP10 propeptides may be produced from naturally occurring or recombinantly produced BMP10 such as standard techniques known in the art, such as by chemical cleavage (e.g., cyanogen bromide, hydroxylamine).

In certain embodiments, the present invention contemplates making mutations in the proteolytic cleavage site of the BMP10 sequence to make the site less susceptible to proteolytic cleavage. The result is a BMP10 polypeptide containing both propeptide and mature portion, which may be useful as an antagonist of BMP10. More preferably, the mature portion is engineered to include a stop codon, such that the BMP10 propeptide is produced with some portion of the mature peptide attached. In one specific embodiment, a mutant may contain one or more point mutations at the following positions of SEQ ID NO: 3: amino acids 313, 314, 315, and 316. In another specific embodiment, such mutant may contain one or more point mutations at the following positions of SEQ ID NO: 4: amino acids 309, 310, 311 and 312.

3. Nucleic Acids Encoding BMP10 Propeptides

In certain aspects, the invention provides isolated and/or recombinant nucleic acids encoding any of the BMP10 propeptides, including functional variants, disclosed herein. For example, SEQ ID NOs: 5 and 6 encode BMP10 propeptides. The subject nucleic acids may be single-stranded or double stranded. Such nucleic acids may be DNA or RNA molecules. These nucleic acids are may be used, for example, in methods for making BMP10 propeptides or as direct therapeutic agents (e.g., in a gene therapy approach).

The subject nucleic acids encoding BMP10 propeptides are further understood to include nucleic acids that are variants of SEQ ID NOs: 5 and 6. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 5 and 6.

In certain embodiments, the invention provides isolated or recombinant nucleic acid sequences that are at least 80%, 85%, 90%, 95%, 97%, 98%, 99% or 100% identical to SEQ ID NO: 5 or 6. One of ordinary skill in the art will appreciate that nucleic acid sequences complementary to SEQ ID NO: 5 or 6, and variants of SEQ ID NO: 5 or 6 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 5 or 6, complement sequence of SEQ ID NO: 5 or 6, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 5-6 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a BMP10 propeptide and operably linked to at least one regulatory sequence. Regulatory sequences are art-recognized and are selected to direct expression of the BMP10 propeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a BMP10 propeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant BMP10 propeptides include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of a subject BMP10 propeptide in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject BMP10 propeptide in cells propagated in culture, e.g., to produce proteins, including fusion proteins or variant proteins, for purification.

This invention also pertains to a host cell transfected with a recombinant gene including a coding sequence (e.g., SEQ ID NO: 5 or 6) for one or more of the subject BMP10 propeptides. The host cell may be any prokaryotic or eukaryotic cell. For example, a BMP10 propeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject BMP10 propeptides. For example, a host cell transfected with an expression vector encoding a BMP10 propeptide can be cultured under appropriate conditions to allow expression of the BMP10 propeptide to occur. The BMP10 propeptide may be secreted and isolated from a mixture of cells and medium containing the propeptide. Alternatively, the propeptide may be retained cytoplasmically or in a membrane fraction and the cells harvested, lysed and the protein isolated. A cell culture includes host cells, media and other byproducts. Suitable media for cell culture are well known in the art. The propeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the propeptide. In a preferred embodiment, the BMP10 propeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant BMP10 propeptide, can allow purification of the expressed fusion protein by affinity chromatography using a $Ni^{2+}$ metal resin. The purification leader sequence can then be subsequently removed by treatment with enterokinase to provide the purified BMP10 propeptide (e.g., see Hochuli et al., (1987) *J. Chromatography* 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies

Another aspect of the invention pertains to antibodies. An antibody that is specifically reactive with a mature BMP10 polypeptide and which binds competitively with the BMP10 propeptide may be used as an antagonist of BMP10 activity. For example, by using immunogens derived from a BMP10 mature peptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the BMP10 peptide, an antigenic fragment which is capable of eliciting an antibody response, or a fusion protein. In a preferred embodiment, the inoculated mouse does not express endogenous BMP10, thus facilitating the isolation of antibodies that would otherwise be eliminated as anti-self antibodies. Techniques for conferring immunogenicity on a protein or peptide include conjugation to carriers or other techniques well known in the art. An immunogenic portion of a BMP10 peptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of a BMP10, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with BMP10 and monoclonal antibodies isolated from a culture comprising such hybridoma cells.

The term "antibody" as used herein is intended to include fragments thereof which are also specifically reactive with a subject BMP10 peptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a BMP10 peptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to a BMP10 peptide may comprise administering to a mouse an amount of an immunogenic composition comprising the BMP10 propeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the BMP10 peptide. Once obtained, a hybridoma can be propagated in a cell culture, optionally in culture conditions where the hybridoma-derived cells produce the monoclonal antibody that binds specifically to the BMP10 peptide. The monoclonal antibody may be purified from the cell culture.

The adjective "specifically reactive with" as used in reference to an antibody is intended to mean, as is generally understood in the art, that the antibody is sufficiently selective between the antigen of interest (e.g., a BMP10 peptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain aspects, the disclosure provides antibodies that bind to a BMP10 propeptide. Such antibodies may be generated much as described above, using a propeptide or fragment thereof as an antigen. Antibodies of this type can be used, e.g., to detect BMP10 propeptides in biological samples and/or to monitor BMP10 propeptide levels in an individual. The level of BMP10 propeptides maybe measured in a variety of sample types such as, for example, in cells, and/or in bodily fluid, such as in whole blood samples, blood serum, blood plasma and urine. In certain cases, an antibody that specifically binds to a BMP10 propeptide can be used to stimulate activity of BMP10, thereby increasing growth of cardiac tissues or cells.

5. Screening Assays

In certain aspects, the present invention relates to the use of the subject BMP10 propeptides to identify compounds (agents) which are agonist or antagonists of the BMP10 propeptides. Compounds identified through this screening can be tested in cardiac tissues, as well as other tissues (e.g., bone, cartilage, muscle and/or neurons), to assess their ability to modulate tissue growth in vitro. Optionally, these compounds can further be tested in animal models to assess their ability to modulate tissue growth in vivo.

There are numerous approaches to screening for therapeutic agents for modulating tissue growth (e.g., cardiac tissues) by targeting the BMP10 propeptides. In certain embodiments, high-throughput screening of compounds can be carried out to identify agents that perturb BMP10 propeptide-mediated effects on cardiac tissue growth, such as which affect activity of BMP10. In certain embodiments, the assay is carried out to screen and identify compounds that specifically inhibit or reduce binding of a BMP10 propeptide to its binding partner (e.g., a mature peptide of BMP10). Alternatively, the assay can be used to identify compounds that enhance binding of a BMP10 propeptide to its binding protein (e.g., a mature peptide of BMP10). In a further embodiment, the compounds can be identified by their ability to interact with a BMP10 propeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of cardiac tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a BMP10 propeptide and its binding protein (e.g., a BMP10 mature peptide).

Merely to illustrate, in an exemplary screening assay of the present invention, the compound of interest is contacted with an isolated and purified BMP10 propeptide which is capable of binding to a BMP10 mature peptide, as appropriate for the intention of the assay. To the mixture of the compound and BMP10 propeptide is then added a composition containing a BMP10 mature peptide. Detection and quantification of BMP10 propeptide complexes provides a means for determining the compound's efficacy at inhibiting (or potentiating) complex formation between the BMP10 propeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified BMP10 mature peptide is added to a composition containing the BMP10 propeptide, and the formation of BMP10 propeptide/mature peptide complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the BMP10 propeptide and its binding protein may be detected by a variety of techniques. For instance, modulation of the formation of complexes can be quantitated using, for example, detectably labeled proteins such as radiolabelled (e.g., $^{32}P$, $^{35}S$, $^{14}C$ or $^{3}H$), fluorescently labeled (e.g., FITC), or enzymatically labeled BMP10 propeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a BMP10 propeptide and its binding protein. Further, other modes of detection such as those based on optical waveguides (PCT Publication WO 96/26432 and U.S. Pat. No. 5,677,196), surface plasmon resonance (SPR), surface charge sensors, and surface force sensors are compatible with many embodiments of the invention.

Moreover, the present invention contemplates the use of an interaction trap assay, also known as the "two hybrid assay," for identifying agents that disrupt or potentiate interaction between a BMP10 propeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a BMP10 propeptide and its binding protein. See for example, Vidal and Legrain, (1999) Nucleic Acids Res 27:919-29;

Vidal and Legrain, (1999) Trends Biotechnol 17:374-81; and U.S. Pat. Nos. 5,525,490; 5,955,280; 5,965,368.

In one specific example, interaction between a BMP10 propeptide and a BMP10 mature peptide can be assayed by making a construct which expresses a FLAG-tagged BMP10 precursor protein. The FLAG-tagged precursor protein is expressed in cells and processed into a BMP10 propeptide and a FLAG-tagged mature peptide. The protein lysates prepared from the cells are then affinity-purified by antibodies against FLAG. Complexes containing a BMP10 propeptide and a BMP10 mature peptide can be determined by the presence of a BMP10 propeptide in these affinity-purified protein samples (e.g., by immunoblot).

In certain embodiments, the subject compounds are identified by their ability to interact with a BMP10 propeptide of the invention. The interaction between the compound and the BMP10 propeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a BMP10 propeptide. This may include a solid phase or fluid phase binding event. Alternatively, the gene encoding a BMP10 propeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for inhibiting growth or proliferation of cardiac tissues and/or cells. Therefore, any compound identified can be tested in whole cells or tissues, in vitro or in vivo, to confirm their ability to modulate growth of cardiac tissues or cells. Various methods known in the art can be utilized for this purpose. See, for example, Teichmann et al., 2004, Dev Genes Evol, 214:96-8; Pashmforoush et al., 2004, Cell, 117:373-386; Chen et al., 2004, Development, 131:2219-31. Also see U.S. Patent Publication No. 2003/0144176.

In one embodiment, the activity of a BMP10 propeptide or its variants may be tested in a cell-based assay. As an example, the effect of a BMP10 propeptide or its variants on proliferative activity in cardiomyocytes may be assessed. As another example, the effect of a BMP10 propeptide variant on gene expression of some cardiogenic factors (e.g., NKX2.5 and MEF2C) may be assessed. In certain cases, such assays are performed in cells or tissues isolated from the developing heart. This may, as needed, be performed in the presence of recombinant BMP10, and cells may be transfected so as to produce BMP10, and the subject BMP10 propeptide variant. In another embodiment, a BMP10 propeptide or its variants may be administered to a mouse or other animal, and cardiac growth may be assessed in vivo, for example, by measuring the thickening of the innermost layer of the walls (e.g., the formation of myocardial ridges or trabeculae).

It is understood that the screening assays of the present invention apply to not only the subject BMP10 propeptides and variants of the BMP10 propeptides, but also any test compounds including agonists and antagonist of the BMP10 propeptides. Further, these screening assays are useful for drug target verification and quality control purposes.

6. Exemplary Therapeutic Uses

In certain embodiments, compositions (e.g., BMP10 propeptides) of the present invention can be used for treating or preventing a disease or condition that is associated with abnormal activity of BMP10. These diseases, disorders, or conditions are generally referred to herein as "BMP10-associated conditions." In certain embodiments, the present invention provides methods of treating or preventing an individual in need thereof through administering to the individual a therapeutically effective amount of a BMP10 propeptide as described above. These methods are particularly aimed at therapeutic and prophylactic treatments of animals, and more particularly, humans.

In one embodiment, the present invention provides methods for treating or preventing heart disorders in a subject. Such methods comprise administering to the subject an effective amount of a BMP10 propeptide. Exemplary heart disorders include, but are not limited to, cardiomyopathy (e.g., cardiac hypertrophy), congenital heart disease, heart failure, myocardial infarction, and any kind of cardiac dysfunction. In certain cases, heart disorders in the methods are associated with an abnormal proliferation activity of cardiomyocytes.

As described herein, a "cardiomyocyte" is a cell of the cardiac muscle that is striated like skeletal muscle, having microscopically visible myofilaments arranged in parallel with the sarcomere. Cardiac muscle can generate its own excitatory impulses from the sino-atrial node, which acts like a biological pacemaker. In this manner, the contracting signal for cardiac muscles originates in the heart itself. However, the autonomic nervous system can exert control over how fast the signals form and propagate through the heart, which regulates the rate of myocardial contraction.

Cardiomyopathy refers to any disease or dysfunction of the myocardium (heart muscle) in which the heart is abnormally enlarged, thickened and/or stiffened, for example, cardiac hypertrophy. As a result, the heart muscle's ability to pump blood is usually weakened. The disease or disorder can be, for example, inflammatory, metabolic, toxic, infiltrative, fibroplastic, hematological, genetic, or unknown in origin. There are two general types of cardiomyopathies: ischemic (resulting from a lack of oxygen) and non-ischemic. Ischemic cardiomyopathy is a chronic disorder caused by coronary artery disease—a disease in which there is atherosclerotic narrowing or occlusion of the coronary arteries on the surface of the heart. Coronary artery disease often leads to episodes of cardiac ischemia, in which the heart muscle is not supplied with enough oxygen-rich blood. Eventually, the heart muscle enlarges from the additional work it must do in the absence of sufficient oxygen-rich blood.

As described herein, congenital heart disease refers to a heart-related problem that is present since birth and often as the heart is forming even before birth. Congenital heart disease may affect the heart, the heart's valves, the veins leading to, or the arteries leading away, from the heart, or the connections between these parts of the body. Congenital heart disease can result in the progressive cardiomyopathy and life-threatening electrophysiological disorders that often continue long after the surgical correction of the structural defects. Certain congenital heart malformations include septal defects, cardiomyopathy, outflow tract defects, hypoplastic left heart, and associated arrhythmias.

As described herein, heart failure generally refers to the inability of the heart to supply sufficient oxygenated blood to meet the metabolic needs of the tissues and cells in a subject. This can be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure". See Braunwald, Heart Disease: a Textbook of Cardiovascular Medicine, 5th edition 1997, W B Saunders Company, Philadelphia Pa., Chapters 13-17. Conditions that could lead to heart failure include, but are not limited to, cardiomyopathy, congenital heart disease or coronary artery disease.

As described herein, cardiac dysfunction is understood to include any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial ischemia and infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). See Braunwald supra.

In certain embodiments, the present invention contemplates use of the subject compounds (e.g., BMP10 propeptides) in combination with other therapeutic modalities. Thus, in addition to the therapies described above, one may also provide to the patient more "standard" pharmaceutical cardiac therapies. Examples of standard therapies include, without limitation, so-called "beta blockers", anti-hypertensives, cardiotonics, anti-thrombotics, vasodilators, hormone antagonists, endothelin antagonists, calcium channel blockers, phosphodiesterase inhibitors, angiotensin type 2 antagonists and cytokine blockers/inhibitors. For example, combinatorial therapies may be achieved by contacting cardiac cells with a single composition or pharmacological formulation that includes both agents, or by contacting the cell with two distinct compositions or formulations, at the same time. Alternatively, one agent may precede or follow administration of the other agent by intervals ranging from minutes to weeks. In embodiments where two or more different kinds of therapeutic agents are applied separately to an individual, one would generally ensure that a significant period of time did not expire between the time of each delivery, such that these different kinds of agents would still be able to exert an advantageously combined effect on the target tissues or cells.

In certain embodiments, the present invention provides methods and therapeutic agents, for example, antagonists of BMP10 propeptides. Such antagonists (inhibitors) of BMP10 propeptides may be used for promoting cardiac tissue growth or regeneration, and thereby for treating heart damages caused by, for example, myocardial infarction. Examples of these antagonists of BMP10 propeptides include, but are not limited to, compounds that disrupt interaction between a BMP10 propeptide and its binding partner (e.g., a BMP10 mature peptide) and antibodies that specifically bind to a BMP10 propeptide.

In certain embodiments, exemplary BMP10-associated conditions may include developmental processes such as the correct formation of various structures or in one or more post-developmental capacities including creation of bone and cartilage. The role of BMP10 in inducing cartilage and/or bone formation was indicated in U.S. Pat. No. 5,637,480. BMP10-associated conditions may also include disorders of cell growth and differentiation such as inflammation, allergy, autoimmune diseases, infectious diseases, and tumors.

In one specific embodiment, the present invention provides methods of inducing bone and/or cartilage formation, preventing bone loss, increasing bone mineralization or preventing the demineralization of bone. For example, an antagonist (inhibitor) of BMP10 propeptide of the present invention may have an application in treating osteoporosis and the healing of bone fractures and cartilage defects in humans and other animals. The identified compounds (agents) that regulate activity of BMP10 propeptides may be useful in patients that are diagnosed with subclinical low bone density, as a protective measure against the development of osteoporosis.

In another specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject BMP10 propeptides may provide an environment to attract bone-forming cells, stimulate growth of bone-forming cells or induce differentiation of progenitors of bone-forming cells. BMP10 propeptides of the invention may also be useful in the treatment of osteoporosis. Further, BMP10 propeptides may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the BMP10 propeptide of the invention in admixture with a pharmaceutically acceptable vehicle, carrier or matrix.

7. Pharmaceutical Compositions

In certain embodiments, compounds (e.g., BMP10 propeptides) of the present invention are formulated with a pharmaceutically acceptable carrier. For example, a BMP10 propeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP10 propeptides which may also optionally be included in the composition as described above, may alternatively or additionally, be administered simultaneously or sequentially with the BMP10 propeptides in the methods of the invention. Preferably for bone and/or cartilage formation, the composition would include a matrix capable of delivering the BMP10 propeptides or other therapeutic compounds to the site of bone and/or cartilage damage, providing a structure for the developing bone and cartilage and optimally capable of being resorbed into the body. For example, the matrix may provide slow release of the BMP10 propeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., a BMP10 propeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more BMP10 propeptides in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., BMP10 propeptides). The various factors include, but are not limited to, amount of bone weight desired to be formed, the site of bone damage, the condition of the damaged bone, the size of a wound, type of damaged tissue, the patient's age, sex, and diet, the severity of any infection, time of administration, and other clinical factors. Optionally, the dosage may vary with the type of matrix used in the reconstitution and the types of compounds in the composition. The addition of other known growth factors to the final composition, may also effect the dosage. Progress can be monitored by periodic assessment of bone growth and/or repair, for example, X-rays, histomorphometric determinations, and tetracycline labeling.

In certain embodiments of the invention, one or more BMP10 propeptides can be administered, together (simultaneously) or at different times (sequentially or overlapping). In addition, BMP10 propeptides can be administered with another type of therapeutic agents, for example, a cartilage-inducing agent, a bone-inducing agent, a muscle-inducing agent, or a neuron-inducing agent. The two types of compounds may be administered simultaneously or at different times. It is expected that the BMP10 propeptides of the invention may act in concert with or perhaps synergistically with another therapeutic agent.

For example, a variety of osteogenic, cartilage-inducing and bone-inducing factors have been described, particularly bisphosphonates. See e.g., European Patent Application Nos. 148,155 and 169,016. For example, other factors that can be combined with the subject BMP10 propeptides include various growth factors such as epidermal growth factor (EGF), platelet derived growth factor (PDGF), transforming growth factors (TGF-α and TGF-β), and insulin-like growth factor (IGF).

In certain embodiments, the present invention also provides gene therapy for the in vivo production of BMP10 propeptides. Such therapy would achieve its therapeutic effect by introduction of the BMP10 propeptide polynucleotide sequences into cells or tissues having the disorders as listed above. Delivery of BMP10 propeptide polynucleotide sequences can be achieved using a recombinant expression vector such as a chimeric virus or a colloidal dispersion system. Preferred for therapeutic delivery of BMP10 propeptide polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the BMP10 propeptide polynucleotide. In one preferred embodiment, the vector is targeted to cardiac cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for BMP10 propeptide polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Mature BMP-10 Binds to BMP-10 Propeptide

BMP-10 propeptide was immobilized on a BiaCore™ chip. The chip was exposed to conditioned media from cells expressing (upper curve) or not expressing (lower curve) BMP10. Significant binding activity was observed in the conditioned media from cells expressing BMP-10, indicating that BMP-10 propeptide binds to the mature portion.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A pharmaceutical preparation comprising:
   a) a polypeptide comprising a bone morphogenetic protein-10 (BMP10) propeptide; and
   b) a pharmaceutically acceptable carrier,
   wherein the BMP10 propeptide comprises an amino acid sequence at least 98% identical to the amino acid sequence of SEQ ID NO: 1, wherein the BMP10 propeptide contains no more than 20 contiguous amino acids of a mature portion of a BMP10 polypeptide and comprises an alteration in the amino acid sequence that alters glycosylation of the BMP10 propeptide relative to the naturally occurring BMP10 propeptide when produced in a mammalian cell, and
   wherein said BMP10 propeptide has one or more of the following characteristics:
   i) binds to mature BMP10 with a Kd of at least $10^{-5}$ M; and
   ii) inhibits BMP10 signaling in a cell.

2. The pharmaceutical preparation of claim 1, wherein the BMP10 propeptide comprises a sequence alteration that decreases proteolytic cleavage of the BMP10 propeptide relative to the naturally occurring BMP10 propeptide.

3. The pharmaceutical preparation of claim 1, wherein said BMP10 propeptide is a fusion protein including, in addition to said BMP10 propeptide domain, one or more polypeptide portions that enhance one or more of in vivo half life, uptake, tissue localization or distribution, formation of protein complexes, and purification.

4. The pharmaceutical preparation of claim 3, wherein said fusion protein includes a polypeptide portion selected from the group consisting of: an immunoglobulin Fc domain and a serum albumin.

5. The pharmaceutical preparation of claim 3, wherein said fusion protein includes a purification subsequence selected from: an epitope tag, a FLAG tag, a polyhistidine sequence, and a GST fusion.

6. The pharmaceutical preparation of claim 1, wherein said BMP10 propeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

7. The pharmaceutical preparation of claim 1, wherein said preparation is substantially pyrogen free.

8. The pharmaceutical preparation of claim 1, wherein the BMP10 propeptide binds to a mature BMP10 polypeptide with a Kd of less than 1 micromolar.

9. A BMP10 propeptide fusion protein comprising: a BMP10 propeptide and an IgG Fc portion; wherein the BMP10 propeptide comprises an amino acid sequence at least 98% identical to the amino acid sequence of SEQ ID NO: 1, wherein the BMP10 propeptide contains no more than 20 contiguous amino acids of a mature portion of a BMP10 polypeptide and comprises an alteration in the amino acid sequence that alters glycosylation of the BMP10 propeptide relative to the naturally occurring BMP10 propeptide when produced in a mammalian cell, and
   wherein said BMP10 propeptide has one or more of the following characteristics:
   i) binds to mature BMP10 with a Kd of at least $10^{-5M;}$ and
   ii) inhibits BMP10 signaling in a cell.

10. The BMP10 propeptide fusion protein of claim 9, wherein the BMP10 propeptide comprises a sequence alteration that decreases proteolytic cleavage of the BMP10 propeptide relative to the naturally occurring BMP10 propeptide.

* * * * *

UNITED STATES PATENT AND TRADEMARK OFFICE
CERTIFICATE OF CORRECTION

PATENT NO.       : 8,772,234 B2
APPLICATION NO.  : 13/442479
DATED            : July 8, 2014
INVENTOR(S)      : Seehra et al.

Page 1 of 1

It is certified that error appears in the above-identified patent and that said Letters Patent is hereby corrected as shown below:

In the claims,

Column 44, claim number 9, line number 38, please replace "$10^{-5M; and}$" with --$10^{-5}$ M; and--

Signed and Sealed this
Twenty-eighth Day of June, 2016

Michelle K. Lee
*Director of the United States Patent and Trademark Office*